United States Patent
Peng

[19]

[11] Patent Number: 5,879,454
[45] Date of Patent: Mar. 9, 1999

[54] FINGER-MOISTENING MEANS FOR FINGERPRINT RECOGNIZING APPARATUS

[75] Inventor: Hsueh-Chih Peng, Taipei, Taiwan

[73] Assignee: Aetex Biometric Corporation, Taiwan

[21] Appl. No.: 115,870

[22] Filed: Jul. 15, 1998

[51] Int. Cl.[6] .................................................. B41K 1/00
[52] U.S. Cl. .................... 118/31.5; 118/244; 118/260; 118/263; 118/268; 427/1; 427/429
[58] Field of Search ................................ 118/31.5, 244, 118/260, 263, 268; 427/1, 429; 356/71; 382/124, 125

[56] References Cited

U.S. PATENT DOCUMENTS

| | | | |
|---|---|---|---|
| 3,960,632 | 6/1976 | Gaines et al. ........................... | 118/31.5 |
| 4,262,623 | 4/1981 | Smith, III et al. ...................... | 118/31.5 |
| 5,721,006 | 2/1998 | Williams ................................. | 118/31.5 |
| 5,737,071 | 4/1998 | Arndt ...................................... | 118/31.5 |

*Primary Examiner*—Laura Edwards

[57] ABSTRACT

A finger-moistening device for fingerprint recognizing apparatus includes: a container filled with a non-volatile oil or liquid in the container, a powder-metallurgy made roller rotatably mounted and capillarily impregnated in the container to form an oil-impregnated roller, and an upper cover covering the container and having an opening for protruding a peripheral portion of the roller outwardly from the cover and the container for spreading a thin layer of oil or liquid onto the finger of a person to be detected to increase the cohesion between the finger and a prism surface of the fingerprint recognizing apparatus for obtaining a clear fingerprint image for a qualified fingerprint recognition.

8 Claims, 5 Drawing Sheets

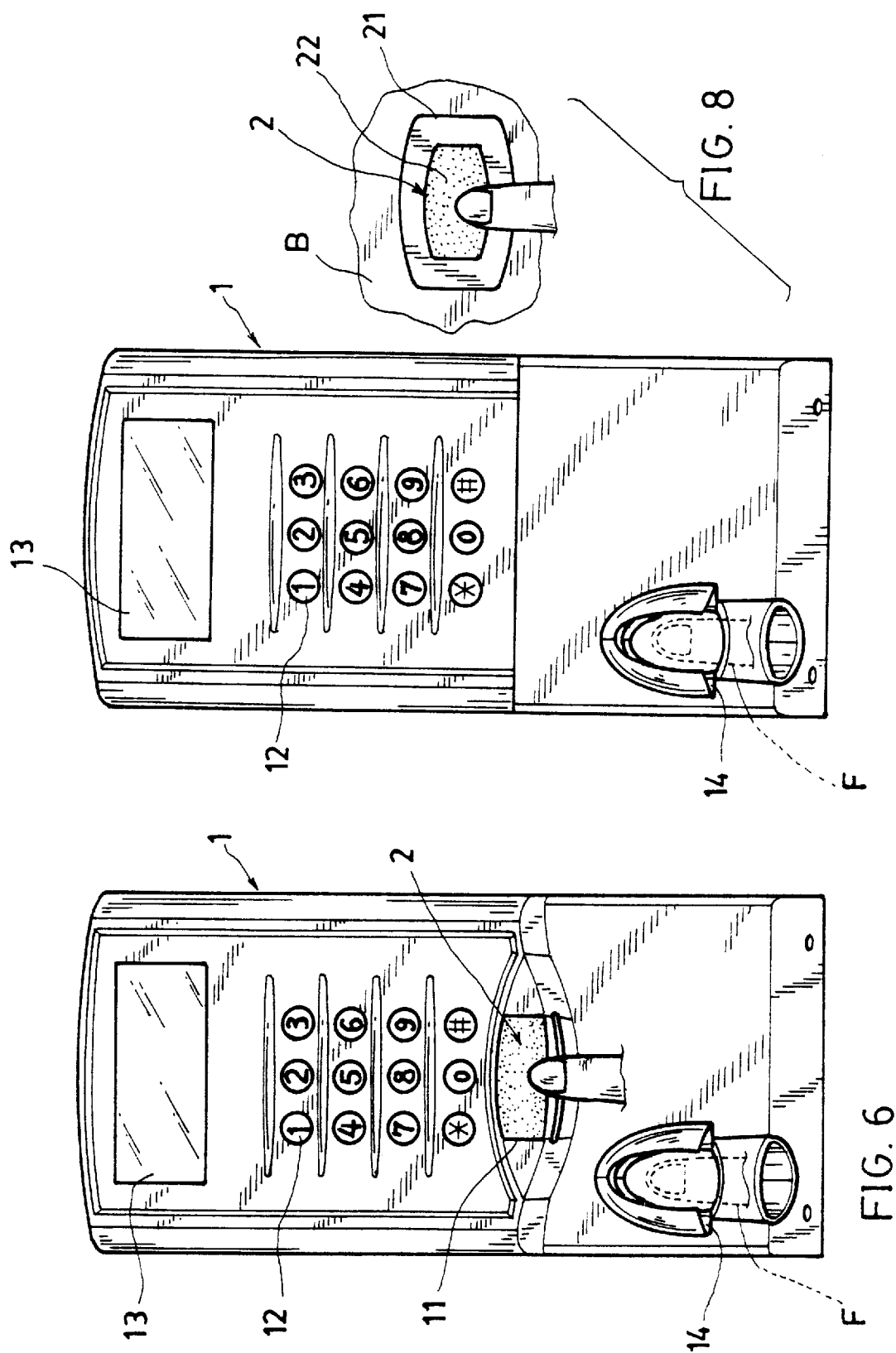

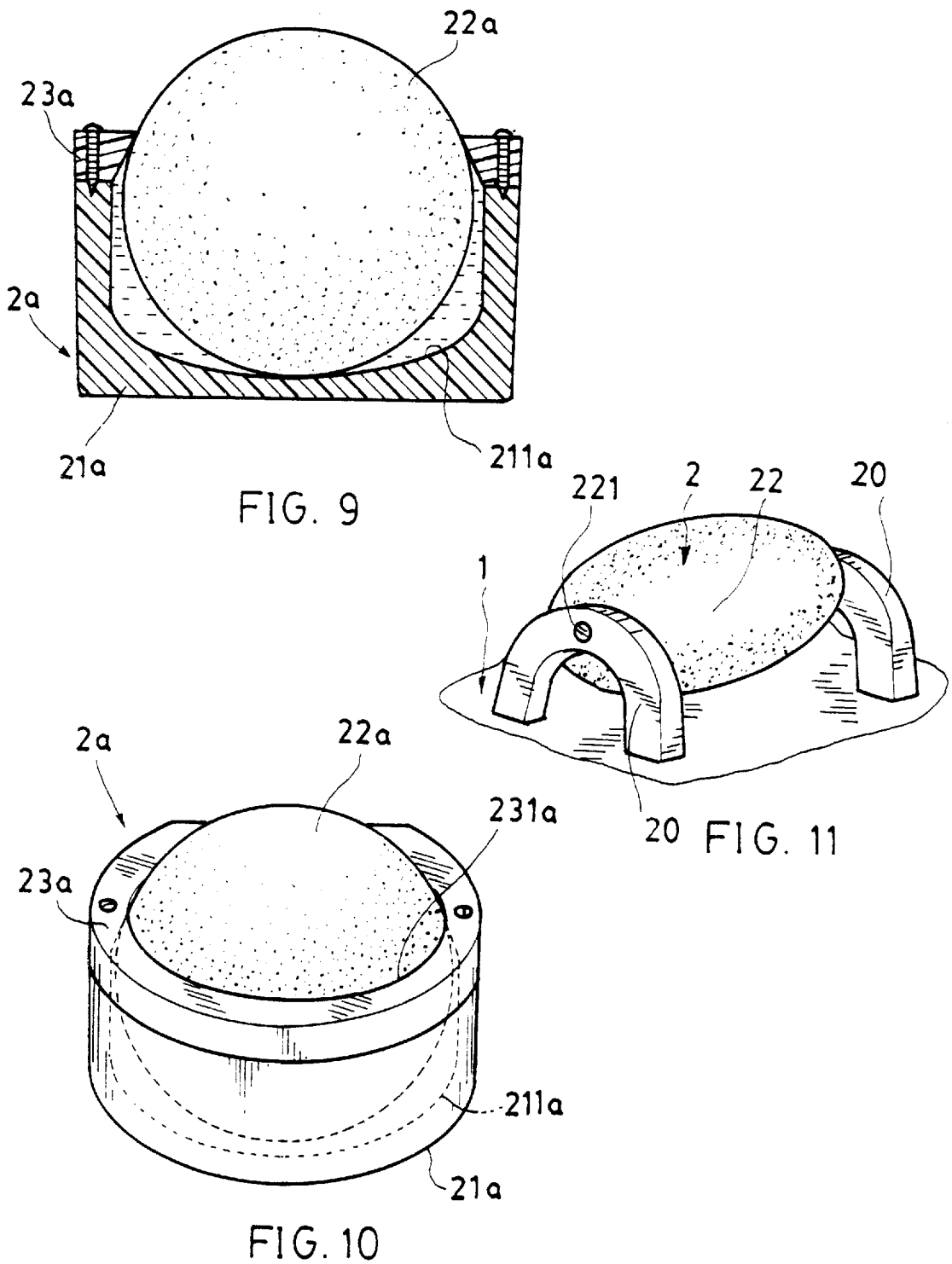

FINGER-MOISTENING MEANS FOR FINGERPRINT RECOGNIZING APPARATUS

BACKGROUND OF THE INVENTION

For recognizing a fingerprint of a person's finger by an optical fingerprint imaging system, the finger is placed on a prism surface whereby the incident light will be absorbed by the ridge of the finger on the finger receiving surface, while the incident light will be internally reflected from the finger receiving surface underneath a valley of the finger, thereby forming fingerprint images having dark areas of the reflection image corresponding to the ridges and having the light areas corresponding to the valleys of the fingerprint.

However, a dry finger has a poor cohesion to the finger receiving surface of the fingerprint recognizing system, the incident light from an illuminator may not be completely absorbed by the ridges of the dry finger and will be partially internally reflected from the finger receiving surface, thereby causing a vague image of the fingerprint and deteriorating the fingerprint identification.

A conventional method to overcome the above-mentioned defect has been tried by moistening the finger with water or alcohol in order to have a closer contact of the finger on the prism surface for making a clear fingerprint image.

Still, the moistening with water or alcohol on the finger has the following drawbacks:

1. The water or alcohol has a good fluidity and is easily volatile to make the contacting areas unclear between the finger and the prism surface. For instance, the water or alcohol may flow from a ridge to a valley to influence the total internal reflection at the valley when touching the finger on the prism surface, thereby deteriorating the image quality of the fingerprint recognition.
2. Even though the water may be soaked in a cotton pad, the water quantity as moistened on the finger from the pad can not be well controlled. Too much water may still contaminate the prism surface and may influence the imaging precision during fingerprint recognition.
3. The wet finger when moistened with water or alcohol may cause dislike feeling for the person to be detected. Meanwhile, the water or alcohol pad should be always maintained or replaced with fresh one for hygienic purpose, causing inconvenience for the maintenance of the fingerprint imaging device.

The present inventor has found the drawbacks of the conventional fingerprint recognition systems and invented the present finger-moistening means for fingerprint recognizing apparatus.

SUMMARY OF THE INVENTION

The object of the present invention is to provide a finger-moistening device for fingerprint recognizing apparatus including: a container filled with non-volatile oil or liquid or paste in the container, a powder-metallurgy made roller rotatably mounted and capillarily impregnated in the container, and an upper cover covering the container and having an opening for protruding a peripheral portion of the roller outwardly from the cover and the container for spreading a thin layer of oil (or liquid or paste) onto the finger of a person to be detected to increase the cohesion between the finger and a prism surface of the fingerprint recognizing apparatus for obtaining a clear fingerprint image for a qualified fingerprint recognition.

BRIEF DESCRIPTION OF THE DRAWINGS

FIG. 6 is a top view illustration of the present invention.

FIG. 8 shows another application of the present invention when used separately from a fingerprint recognizing apparatus.

FIG. 9 is a perspective view of another preferred oil spreading means of the present invention.

FIG. 10 is a sectional drawing of FIG. 9.

FIG. 11 shows further preferred embodiment of the present invention.

DETAILED DESCRIPTION

Figure 1:
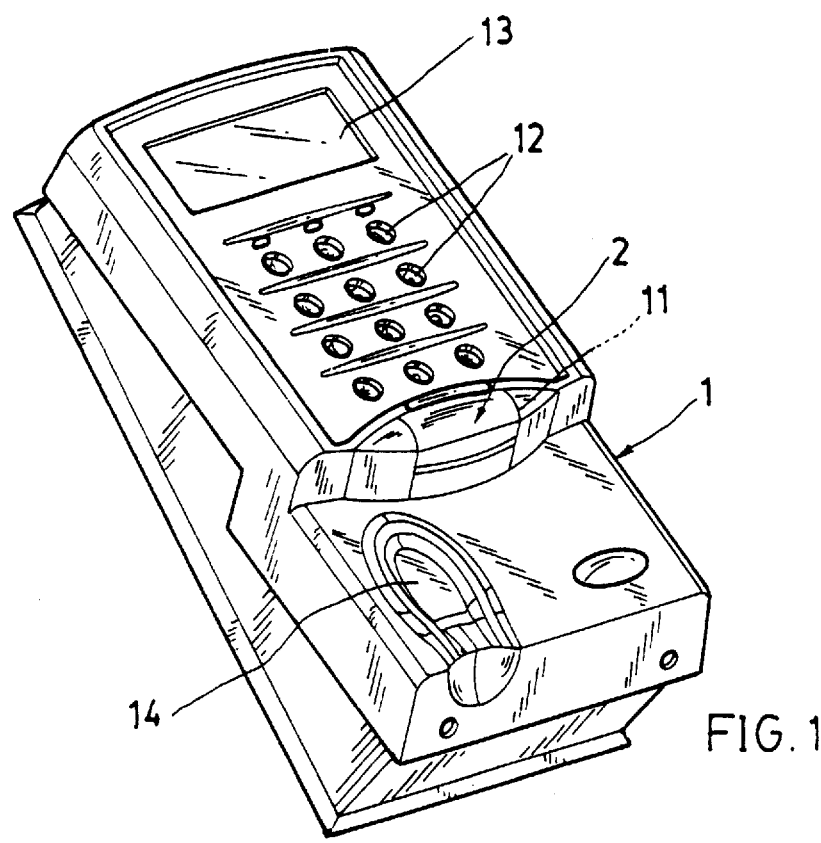
FIG. 1 is a perspective view of the present invention when secured on a fingerprint recognizing apparatus.
Figure 2:
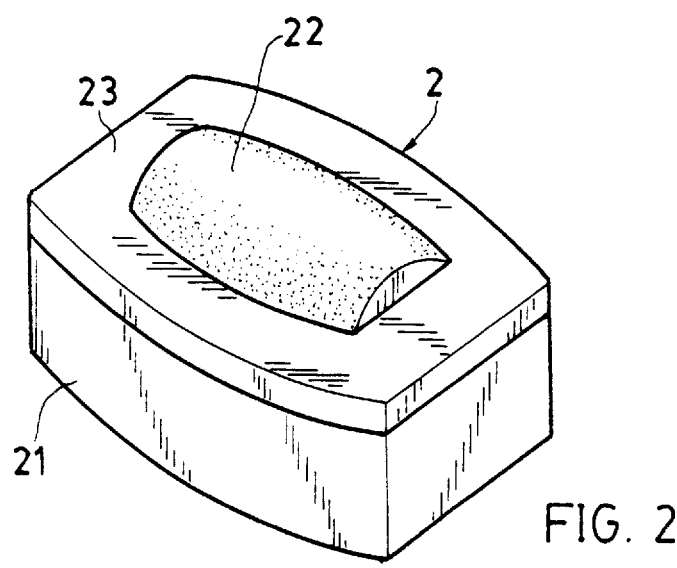
FIG. 2 is a perspective view of the present invention.
Figure 3:
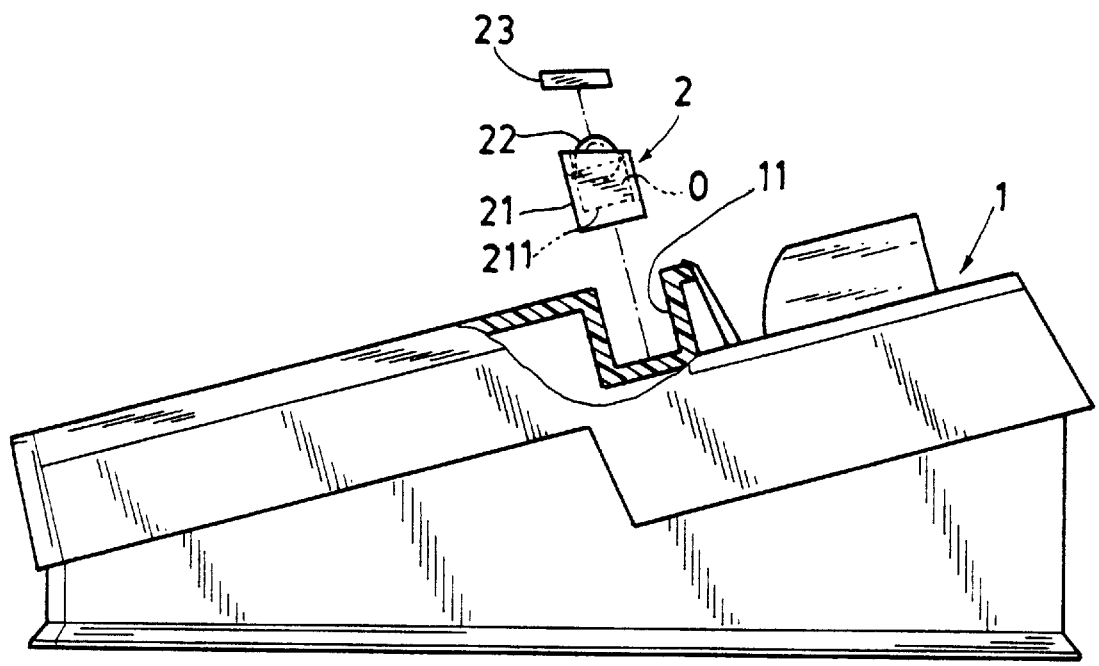
FIG. 3 is a side-view illustration of the present invention to be secured on a fingerprint recognizing apparatus.

As shown in FIGS. 1–7, the present invention for use on a fingerprint recognizing apparatus 1 comprises a finger-moistening means 2 which is secured, adhered, embedded or attached on the fingerprint recognizing apparatus 1. The finger-moistening means 2 may also be placed on any supporting base or surface B as shown in FIG. 8 to be separated from the fingerprint recognizing apparatus 1, not limited in the present invention.

The finger-moistening means 2 may be embedded, fixed or engaged in a trough 11 recessed in an upper or top surface of the fingerprint recognizing apparatus 1.

The fingerprint recognizing apparatus 1 includes a plurality of keys 12 resiliently provided on the recognizing apparatus for keying in an identification code of a person to be detected, a display 13 for showing the information (such as the recognizing result) of the fingerprint recognition on the display, and a prism 14 having a finger surface S on a top surface of the prism to be touched by a finger of the person to be detected for sensing a fingerprint image from the finger to be compared with that as pre-stored in the recognizing apparatus for fingerprint recognition and identification. The fingerprint recognizing apparatus or imaging system is a conventional optical electronic fingerprint device and is therefore not described in detail herewith. The present invention can be used on any types or models of the fingerprint recognizing or imaging devices.

The finger-moistening means 2 includes a container 21 having a pool 211 recessed in the container 21 for filling oil, liquid or paste in the pool 211; a powder-metallurgy made roller 22 having a pivot 221 rotatably on a pivot holder 20 fixed in the container 21; and an upper cover 23 having an opening notched is the cover 23 for protruding a partial peripheral of the roller 22 upwardly or outwardly for spreading a finger of a person to be detected.

The powder-metallurgy made roller 22 is a porous and oil (or liquid or paste) permeable medium (such as made of copper or metal powder) having a lower portion thereof soaked with the oil or liquid 0 in the pool 211 of the container 21 for impregnating oil or liquid into the roller 22 especially on the roller circumferential surface to be spread on a finger of a person to be detected.

The roller 22 may also be modified to be a non-rotatable powder metallurgy pad, not limited in the present invention. The pad is then soaked in the pool 211 of the container 21. The roller or pad, if pre-impregnated with oil or liquid therein, the container 21 may then be eliminated.

The oil O may be selected from: petroleum oil, mineral oil, animal oil, plant oil, or mixing oils; or may be substituted with other oil-like liquid or paste; having lower volatility (higher boiling point) and higher viscosity than that of water and ethyl alcohol.

Figure 5:
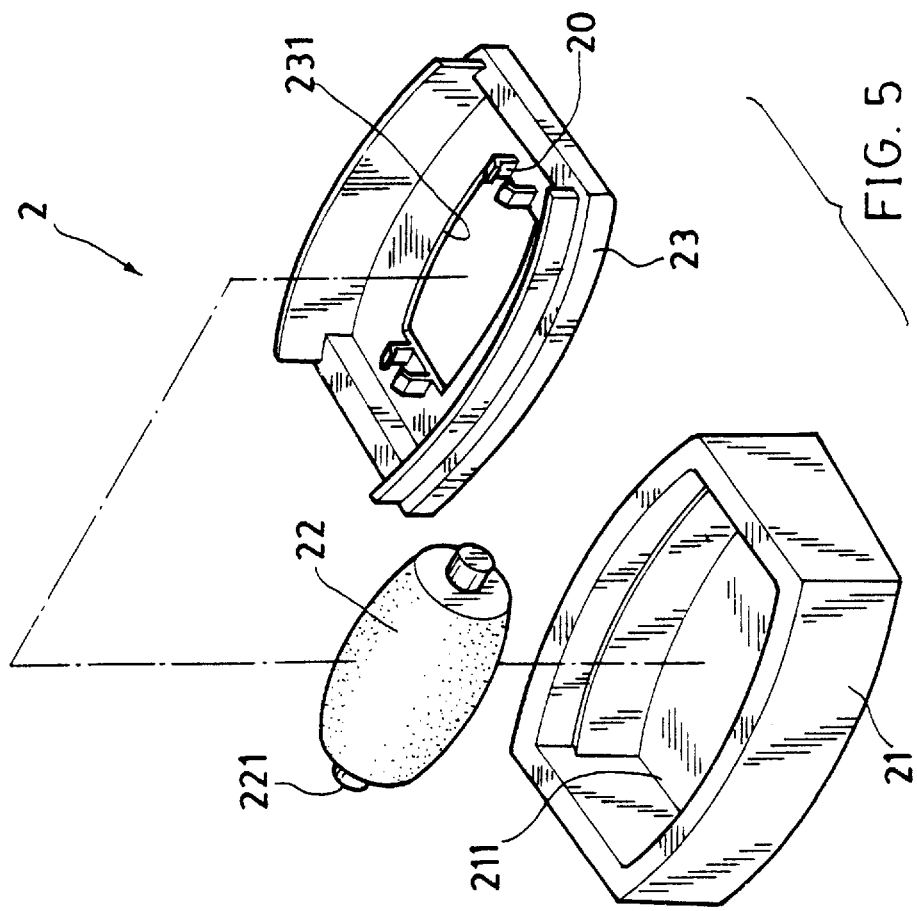
FIG. 5 shows another preferred embodiment of the present invention.
Figure 4:
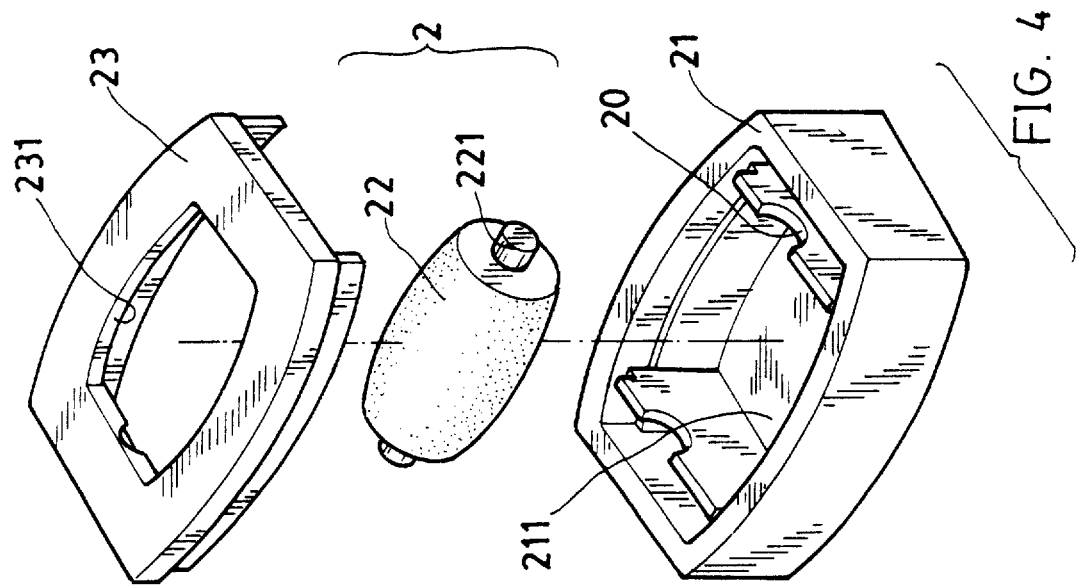
FIG. 4 is an exploded view of the present invention.

The pivot holder 20 is formed with pivot hole to be engageable with the pivot 221 of the roller 22, The pivot holder 20 is integrally formed in the container 21 as shown in FIG. 4. Or, the pivot holder 20 may be integrally formed on an inside wall of the upper cover 23 as shown in FIG. 5 for rotatably engaging the pivot 221 of the roller 22 so that the roller 22 will then be rotatably mounted in the container 21. Other modifications of the pivot holder 20 may be made for the present invention.

The finger-moistening means 2 may be modified to be a powder-metallurgy made ball 22a universally mounted in an oil-filled pool 211a within a container 21a covered with an upper cover 23a formed with a circular opening 231a in the cover 23a for providing the ball 22a outwardly or upwardly for spreading a finger.

Figure 7:
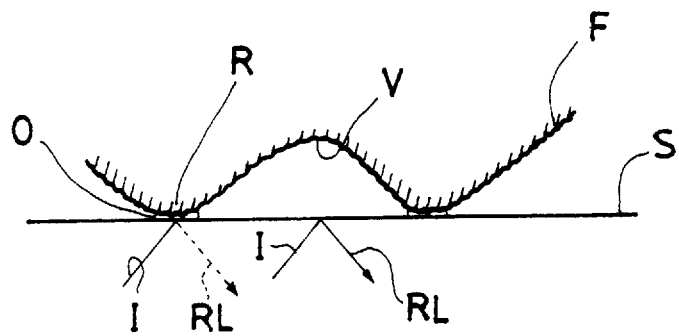
FIG. 7 is an illustration showing the operation principle of the present invention.

Once the roller 22 or ball 22a rotatably mounted in the container 21, the oil or liquid O will be impregnated into the porous powder-metallurgy made roller or ball. Upon touching of a finger on the roller or ball surface, the oil or liquid will be spread onto the finger with merely a thin layer of oil or liquid for increasing a cohesion between the ridges R of the finger F and the finger receiving surface S as shown in FIG. 7. Then, the finger F is placed on the finger receiving surface or prism surface S of the prism 14 as shown in FIG. 6 (or 8) for fingerprint identification.

The incident light I from an illuminator in the fingerprint recognizing apparatus 1 as projected to the ridge R of the finger F will be substantially completely absorbed by the ridge R since the small void aperture between the finger receiving surface or prism surface S and the ridge R has been filled with oil (O) so as to greatly minimize the total internal reflection (RL) as dotted line shown in FIG. 7 to reveal a dark area in the fingerprint image. The total internal reflection RL as reflected from another incident light I underneath the valley V of the finger F will indicate a light area of the fingerprint image for forming the fingerprint image very clearly for increasing the precision and reliability of the fingerprint recognition.

The present invention in superior to the conventional fingerprint imaging systems by moistening water or alcohol on the finger with the following advantages:

1. The oil or liquid or paste is viscous and non-volatile to increase the cohesion between the finger and the prism surface for making a clear image with distinguished ridge (dark) area and valley (light) area.
2. The oil or liquid as spread to the finger only requires a little quantity which will not contaminate the prism surface S for an easy and hygienic maintenance.
3. Only a thin layer of oil or liquid is coated on the person's finger without causing dislike feeling for the person to be detected.
4. The oil or liquid is not volatile and only consumed a little quantity for each test so that the refilling of oil may be prolonged.

The present invention may be modified without departing from the spirit and scope of the present invention.

As shown in FIG. 11, the roller 22 may be pivotally mounted in a pivot holder 20 including a pair of brackets fixed on a fingerprint recognizing apparatus 1. The cover 23 and the container 21 may also be eliminated.

The roller 22 may be rotatably mounted on the apparatus 1 or just embedded or fixed on the apparatus 1.

Other fluids for substituting the oil such as a liquid or paste should have a higher viscosity and boiling point than that of water and ethyl alcohol.

I claim:

1. A finger-moistening means for fingerprint recognizing apparatus comprising:

a container having a non-volatile fluid filled in said container, said fluid having a viscosity and boiling point higher than that of water and ethyl alcohol;

a powder-metallurgy made medium held in said container and having a lower portion of said powder-metallurgy made medium soaked in said fluid in said container to be capillarily impregnated with said fluid in said medium; and an upper cover covering said container and having an opening formed in said cover for protruding an upper peripheral portion of said power-metallurgy made medium outwardly for spreading said fluid as impregnated in said medium to a finger of a person to be detected on a fingerprint recognizing apparatus to increase a cohesion between the finger and a finger receiving surface of a prism of said fingerprint recognizing apparatus for forming a clear fingerprint image.

2. A finger-moistening means for fingerprint recognizing apparatus according to claim 1, wherein said container is securable on a fingerprint recognizing apparatus.

3. A finger-moistening means according to claim 1, wherein said fluid is an oil and selected from: a petroleum oil, mineral oil, animal oil, plant oil, and mixing oils thereof and having a viscosity and a boiling point greater or higher than that of water and ethyl alcohol.

4. A finger-moistening means according in claim 1, wherein said container has a pool recessed in the container for filling said fluid in the pool; and said powder-metallurgy made medium being a powder-metallurgy made roller rotatably mounted in the container.

5. A finger-moistening means according in claim 4, wherein said roller includes a pivot rotatably engageable with a pivot holder for rotatably mounting said roller thereon.

6. A finger-moistening means according in claim 1, wherein said powder-metallurgy made medium is a non-rotatable powder-metallurgy pad as soaked in an oil-filled pool in the container.

7. A finger-moistening means according in claim 1, wherein said powder-metallurgy made medium is a powder-metallurgy made ball universally mounted in an oil-filled pool within said container covered with said upper cover formed with a circular opening in the cover for protruding the ball outwardly for spreading oil from said ball to a finger.

8. A finger-moistening means for fingerprint recognizing apparatus comprising:

a powder-metallurgy made roller pre-impregnated with a fluid having a viscosity and boiling point higher than that of water and ethyl alcohol, and wherein said roller is pivotably mountable on a fingerprint recognizing apparatus for spreading the fluid to a person's finger to increase a cohesion between the finger and a finger receiving surface of the fingerprint recognizing apparatus for forming a clear fingerprint image.

\* \* \* \* \*